(12) United States Patent
Cole Warren

(10) Patent No.: US 6,471,193 B2
(45) Date of Patent: Oct. 29, 2002

(54) AUTOMATED ODOR MODIFIER

(76) Inventor: Jacqueline M. Cole Warren, 4211 St. Michael's Ct., Sugar Land, TX (US) 77478

( * ) Notice: Subject to any disclaimer, the term of this patent is extended or adjusted under 35 U.S.C. 154(b) by 19 days.

(21) Appl. No.: 09/778,153

(22) Filed: Feb. 5, 2001

(65) Prior Publication Data

US 2002/0105099 A1 Aug. 8, 2002

(51) Int. Cl.[7] .................................................. B01F 3/04
(52) U.S. Cl. ........................... 261/27; 261/95; 261/101; 261/DIG. 88
(58) Field of Search ............................ 261/26, 27, 28, 261/95, 96, 97, 101, 102, 105, DIG. 65, DIG. 88; 96/222, 397, 399, 424

(56) References Cited

U.S. PATENT DOCUMENTS

| | | | | |
|---|---|---|---|---|
| 3,633,881 A | * | 1/1972 | Yurdin ................ | 261/DIG. 65 |
| 4,702,418 A | * | 10/1987 | Carter et al. ................ | 239/101 |
| 5,023,020 A | * | 6/1991 | Machida et al. ..... | 261/DIG. 65 |
| 5,223,182 A | * | 6/1993 | Steiner et al. ................ | 261/26 |
| 5,449,117 A | * | 9/1995 | Muderlak et al. ............... | 239/6 |
| 5,542,964 A | * | 8/1996 | Kroeger et al. .................. | 95/6 |
| 5,591,409 A | * | 1/1997 | Watkins ...................... | 422/110 |
| 5,882,256 A | * | 3/1999 | Shropshire .................. | 454/157 |

* cited by examiner

Primary Examiner—C. Scott Bushey

(57) ABSTRACT

An Automated Odor Modification System 10 is provided having an electronic programmable timer 100, a container liquid level detector 150, a nozzle liquid level detector 140, a motor control circuit 108, an electric motor 126, a liquid container 200, a housing for the enclosure 300, a nozzle 230, a fan 85, and tubing 220. When 200 has sufficient liquid; 230 has insufficient liquid; 100 is set to the date and time to come on: motor 126 pumps liquid into the nozzle 230 via 220. Fan 85 is used to transfer the vapors of the odor modification liquid from 230 to the desired locations. The fan 85 keeps running until the electronic programmable timer completes its cycle. The system is designed so that if the liquid in container 200 is insufficient; the system will be deactivated until the level of the liquid therein, is brought into specification.

7 Claims, 3 Drawing Sheets

AUTOMATED ODOR MODIFIER

TECHNICAL FIELD

This invention relates to an Automated Odor Modifier and more particularly to an Automated Odor Modifier to be used to facilitate the elimination of objectionable odor within living, working and recreation spaces. Because the imprecise release of pleasant odors can become objectionable, this system electronically times, meters, and release pleasant odor modification vapors into the selected locations via a fan. The pleasant odor modification liquids are stored in containers, and are pumped to nozzles in the selected locations. This invention vastly reduces the need for localized air freshener substances, devices, or aerosol sprays.

BACKGROUND ART

Throughout the years, many attempts have been made, to eliminate indoor malodor, but with only marginal success. A very good attempt was made by Kroeger at al., U.S. Pat. No. 5,542,964. In this invention Electrostatic and Radio Frequency signals are used to remove the airborne contaminants that contributes to malodor. Although this invention seems effective in some applications, it is too complicated to be useful in most applications. Additionally, because Radio Frequency (R.F.) signals can interfere with so many electronic instruments found in today's living, working, and recreational spaces; this method is unattractive.

Another worthwhile attempt in this endeavor was made by Carl Watson, U.S. Pat. No. 5,591,409. The delivery system disclosed by Watkins is very cumbersome and inefficient. Watkins teaches a delivery system in which pressurized cans are placed in an enclosure, the aroma within the cans is expelled by electromechanical means. Clearly this system is a high maintenance system suitable only for entertainment venues.

SUMMARY OF INVENTION

This invention relates to an Automated Odor Modification System used for automatically, and precisely releasing odor modification agents in liquid vapor form into the selected spaces. The odor modification liquids are stored in containers; and are delivered to the desired locations based upon the setting of an electronic programmable timer; liquid level of the containers, and nozzle reservoirs. Each location can be programmed for service independently of each other. For example four locations can received four different odor modification agents simultaneously.

BEST MODE FOR CARRYING OUT THE INVENTION

Figure 1:
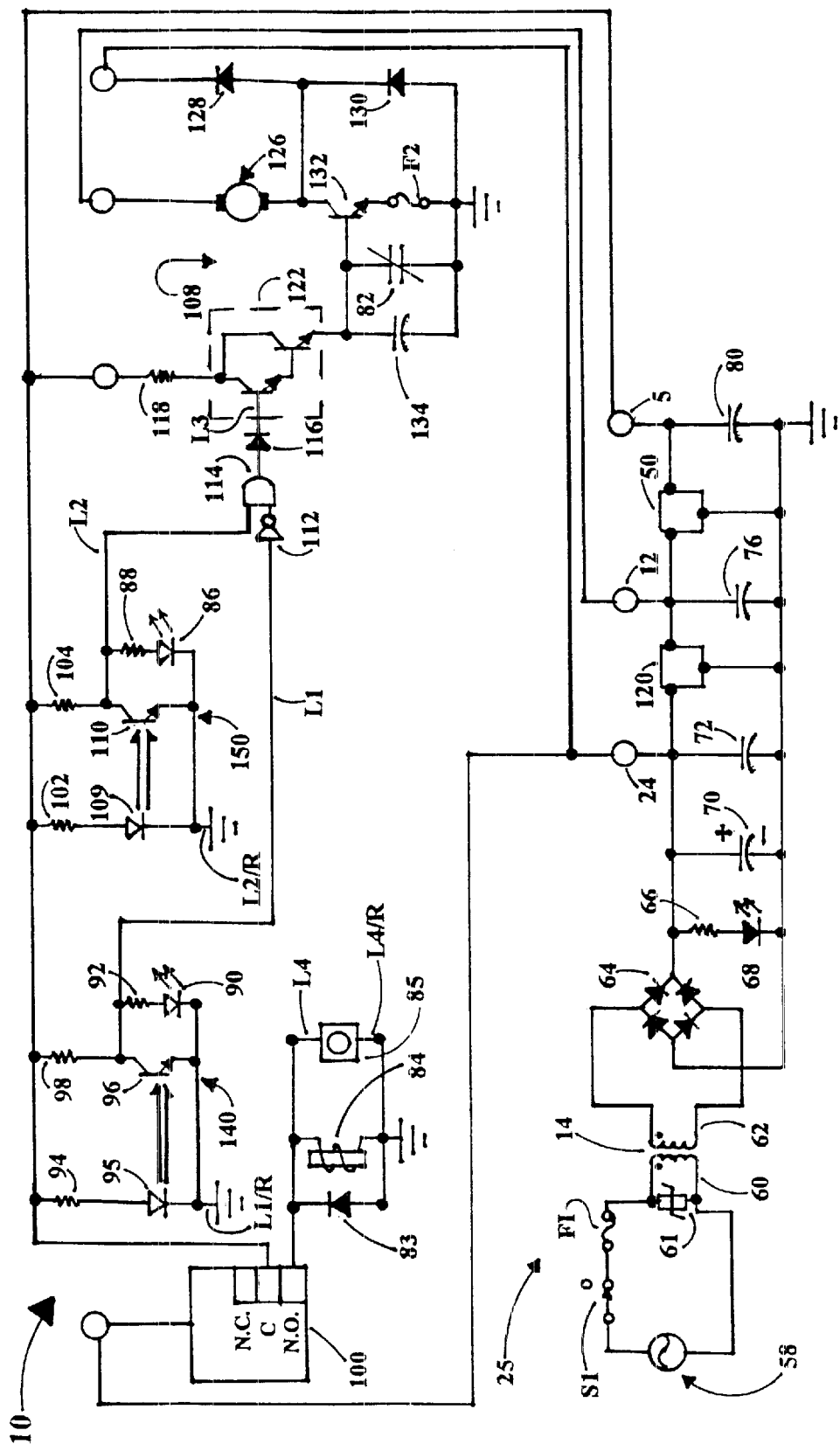
FIG. 1 is an electronic schematic diagram showing one zone of the Automated Odor Modification System in accordance with the principles of this invention.

In FIG. 1 there is shown, an Automated Odor Modification System, generally designated by the numeral 10. The Automated Odor Modification System 10 includes a primary DC power source, generally designated by the numeral 25; a 24 Volts DC power terminal, generally designated by the numeral 24, a 12 Volts Regulated DC power terminal, generally designated by the numeral 12. A 5 Volts regulated DC power terminal, generally designated by the numeral 5 is also provided. The 24 volts DC power terminal 24 is connected to the electronic programmable timer, generally designated by the numeral 100; and transistor 132 transient suppression circuit. The DC power terminal 12 is connected to the pump motor, generally designated by the numeral 126. The DC power terminal 5 is connected to the following circuits: The liquid level detector at the container, generally designated by numeral 150; The liquid level detector at the nozzle, generally designated by the numeral 140; The motor control circuit, generally designated by the numeral 108, and the C terminal of 100.

The DC power source 25 of the Automated Odor Modification System 10 is equipped with a power transformer 14, having primary windings 60 and secondary windings 62. A rectifier 64 is provided to convert alternating current (ac) power to direct current (DC) power. Capacitors 70, 72, 76, and 80 are provided to filter out the ripple. Voltage regulator 120 is provided to furnish 12 Volts regulated DC power, while Voltage regulator 50 provides 5 Volts regulated DC power. Light emitting diode (LED) 68 is connected in series with resistor 66, to form the power on indicator. Power switch S1 is provided to connect the ac power source 58 to the primary windings of power transformer 14. Varistor 61 provides voltage transient suppression means when as power source 58 is connected or disconnected. Fuse F1 is provided for over current protection.

Electronic programmable timer 100 is provided to control the time and date for the release of odor modification vapor. Nozzle liquid sensor 140 is comprised of 90,92,94,95,96, and 98; Container liquid level detector 150 is comprised of 876,88,102,104,109, and 110; Motor control circuit 108 is comprised of 82,84,112,114,116,118,122,132, and 134. Diodes 128 and 130 are provided to protect 132 from transient. Nozzle fan 85 and relay 84 are energized when 100 is activated. Diode 83 is used to suppress the transients generated by 84.

Figure 2:
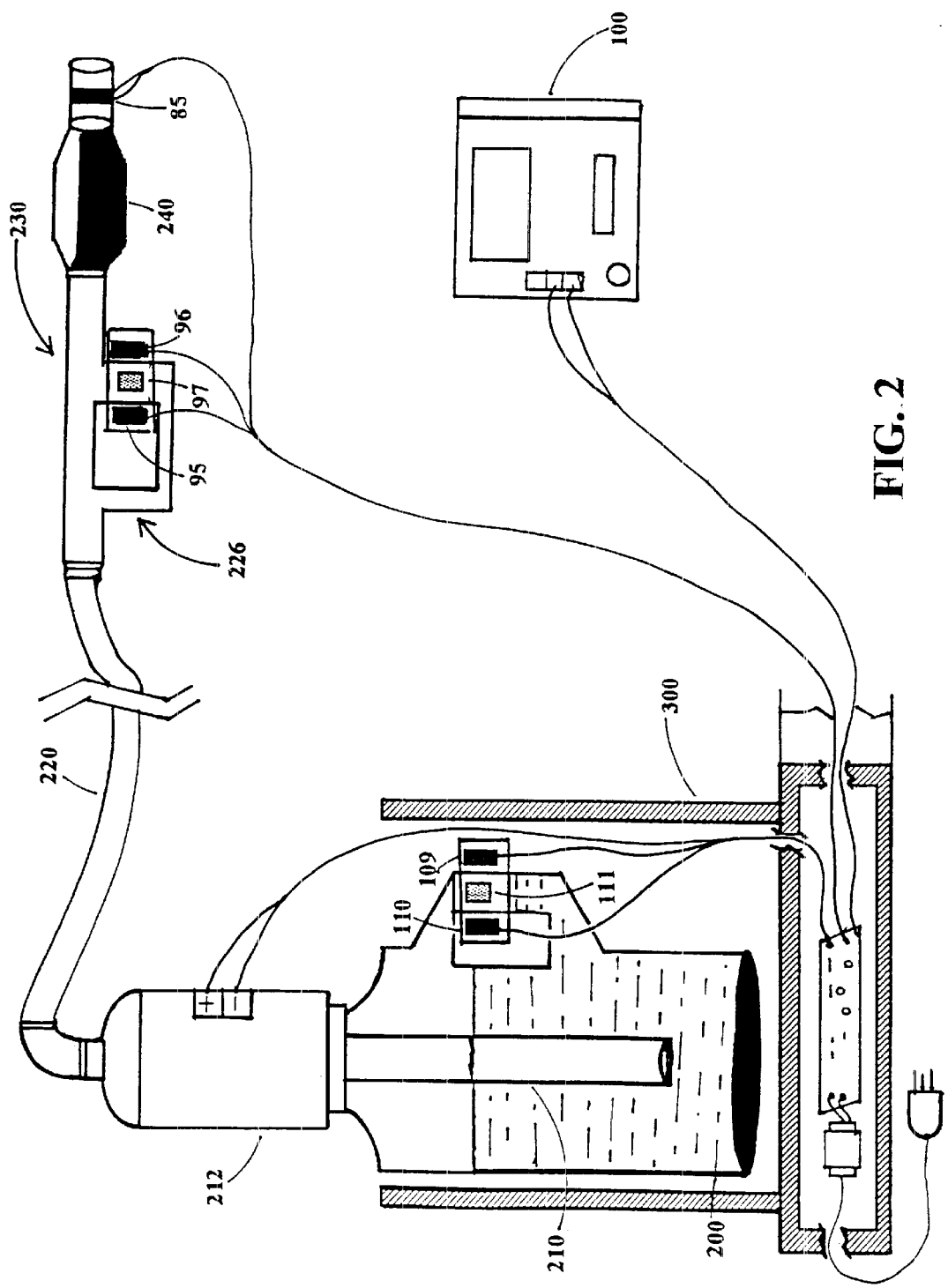
FIG. 2 is a pictorial diagram of the Odor Modification System showing electrical interconnections of FIG. 1 in accordance with the principles of this invention.

Referring to FIG. 2 there is shown a Pictorial representation of the liquid delivery system of the Automated Odor Modification System in accordance with this invention. Liquid container, generally designated by the numeral 200 stores the odor modifying agents to be dispensed. Container 200 is fitted into an enclosure, generally designated by the numeral 300; having an opening at the top, and a compartment at the bottom to facilitated electrical connections. Pump housing, generally designated by the numeral 212, houses pump motor 126, and is affixed to the neck of 200. Pump housing 212 has siphon tube 210 connected to it's input; tubing 220 to it's output; and terminals to facilitate the electrical connections of the pump motor 126. Also shown is the nozzle generally designated by the numeral 230, that houses 95,96, buoyant material 97; liquid absorbent material 240 and fan 85. Shown affixed to the handle of 200 are components of the container liquid level detector circuit; namely 109, 110, and buoyant material 111.

Figure 3:
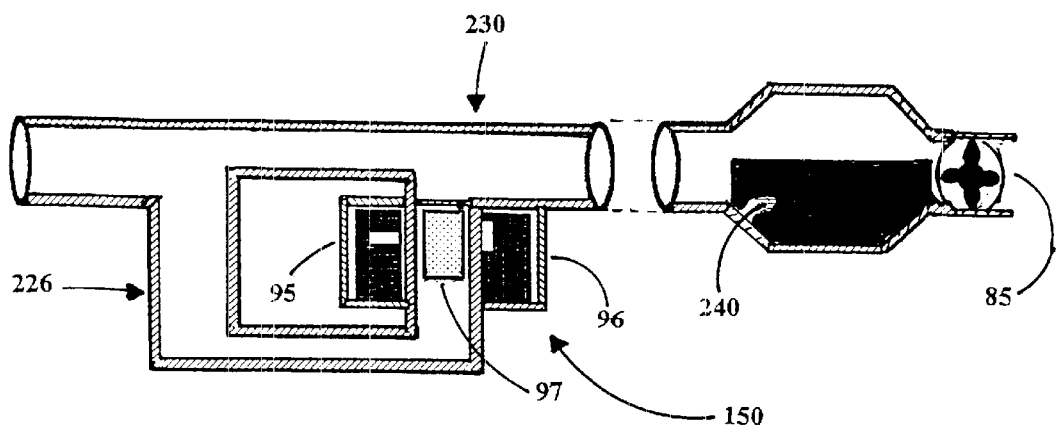
FIG. 3 is a detailed pictorial diagram showing the nozzle depicted in FIG. 2 in accordance with the principles of this invention.

Referring to FIG. 3 there is shown a detailed pictorial representation of the nozzle 230 in accordance with this invention. Reservoir 226 stores the odor modifying liquid pumped from the container 200. Liquid absorbent material 240 is located behind fan 85. Fan 85 is used to transfer liquid vapor into the selected location. Reservoir liquid level detector 150 is comprised of photon transmitter 95, photon receiver 96, and buoyant material 97. Nozzle 230 is made of translucent material.

Figure 4:
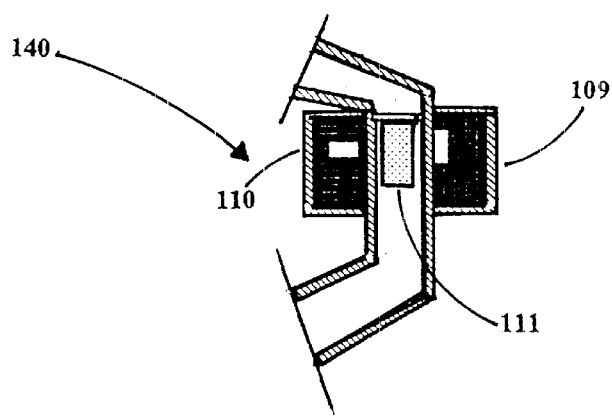
FIG. 4 is a detailed pictorial diagram showing the container liquid level detection circuit depicted in FIG. 2 in accordance with the principles of this invention.

Referring to FIG. 4 there is shown a detailed pictorial representation of the container liquid level detection circuit 140 in accordance with this invention. Container level detector 140 is comprised of photon transmitter 110, photon receiver 109, and buoyant material 111. The handle of container 200 is made of translucent material.

To operate the Automated Odor Modification System 10; container 200 is filled with odor modifying liquid; fitted with 212 then placed into 300; then all connections shown in FIG. 2 are made. The system is connected to a 120 volts ac power source 58, then switch S1 is closed. With switch S1 closed, the primary windings 60 of power transformer 14 are energized causing power to be transferred magnetically to its secondary windings 62. A stepped down version of the ac voltage applied across 60 is transferred across rectifier 64 via 62. Rectifier 64 converts the ac power to pulsating DC power, then capacitors 70 and 72 filters the pulsating DC power, thereby producing a relatively pure DC power at terminal 24. The voltage at terminal 24 causes current to flow through resistor 66, then through LED 68 causing it to light. DC Voltage regulator 120 converts the unregulated DC power seen at terminal 24 and transforms it into regulated DC power seen at terminal 12 to regulated DC power seen at 5. Capacitors 76 and 80 are used for ripple suppression. The DC power available at the following terminals are as follows: 24=24 volts, 12=12 volts, 5=5 volts. At the moment that switch S1 is closed, 100,140,150, and 108 are energized; and +5 vDC is available at the C terminal of 100. The energizing of 100,140,150, and 108 causes several things to happen simultaneously: current flows from 5 through 95 to ground, via series resistor 94, causing 95 to turn on, thereby emitting photons in the direction of 96; 150 is also energized causing current to flow from 5 through 109 to ground via series resistor 102. This current path causes 109 to turn on, thereby emitting photons in the direction of 110. Although the aforementioned circuits are energized, the system remains dormant until the electronic programmable timer 100 is activated.

The electronic programmable timer 100 is now set to come on and go off at preset times. The initial action of 100, connects its C contact to its N.O. contact, thereby connecting 83,84 and 85 to 5. At the instant power is applied to the aforementioned components, current flows out of N.O. through 84 to ground, causing 84 to be energized; this opens 82; 83 is used for transient suppression. N.O. also supplies power to 85, causing it to rotate. Although the system is programmable to come on, the status of 140 and 150 controls the dispensation of odor modification liquid.

If 200 has sufficient liquid therein; the buoyant material 111 rises to a level where it is situated between 110 and 109; thereby blocking the photons emitted by 110 from reaching 109 via the translucent material from which the handle of 200 is fabricated. Since 111 blocks the photons from getting to 110, 110 remains in the "off state"; which causes the following events to take place: Current flows from 5 through 104, 88, 86, LR/2 to ground; causing 86 to light, thereby indicating that 200 has sufficient liquid; while simultaneously placing a logical high on L2. If insufficient liquid was in 200, 110 would be in the "on state" causing no light to be emitted from 86, and a logical low seen at L2.

If 226 has sufficient liquid therein; the buoyant material 97 will raise to a level where it blocks the photons emitted by 95 from getting to 96 via the translucent material from which 226 is made. Since 97 blocks the photons from getting to 96, 96 stays in an "off state"; which causes the following events to take place: current flows from 5 through 98, 92, 90, LR/1 to ground; causing 90 to light, thereby indicating that 226 has sufficient liquid; while simultaneously placing a logical high on L1. If insufficient liquid was in 226, 92 would be in the "on state" causing no light to be emitted from 90, and a logical low seen at L1.

The system will transfer liquid if and only if, the electronic programmable timer 100 is set; container 200 has sufficient liquid; nozzle reservoir 226 has insufficient liquid. When the three conditions mentioned above are met, then the following occurs: The photons emitted from 95 reaches 96 since 97 is not in the path of the photons; 96 is driven into the "on state"; 92 is not illuminated; a logical low is placed on L1. With a logical low at the input of 112 via L1; 112 inverts this logical low to a logical high; thereby placing a logical high at one input of AND gate 114. At this point 114 having a logical high on each input, place a logical high on its output, which causes 116 to become forward biased. With 116 forward biased the following events occurs: a logical high is placed at the base of 122 via L3, driving 122 into the "on state"; current flows from 5 through 118 and 122, causing current to flow into the base of 1132. Current flowing into the base of 1 causes the following to occur: 132 is driven into the "on state" which causes current to flow from 12 through 126, 132, and F2 to ground; current flowing through 126 causing it to rotate. The rotation of 125 causes liquid stored in 200 to be drawn into 210, then pumped to 230 via 212 and 220. If the liquid enters 230 in a stream, liquid absorbent material 240 prevents this stream from exiting 230 by blocking it; thereby causing the liquid to flow into 226. The migration of liquid into 226 continues until 97 rises, blocking the photons from 95 getting to 96. At this point a logical high is seen at L1, which is the input of 112; 112 inverts this logical high to a logical low; And gate 114 has a logical high on one input and a logical low on the other, causing a logical low o be present at its output. A logical low at the output of 114 initiates the following events: 116 is no longer forward biased; 122 and 132 are drivent into the "off state"; 126 ceases to rotate since 132 is in the "off state". At this point the pumping of liquid ceases and 85 continues to blow the odor modification vapors into the desired spaces. The cycle continues until the electronic programmable timer 100 times out.

What is claimed is:

1. An odor modification system comprising:
   an enclosure having an opening formed therein;
   a container within said enclosure, said container holding a first quantity of odor modifying liquid;
   a nozzle including a fan for dispensing odor modifying liquid to a selected location in the form of a vapor;
   liquid transport means for transporting liquid from said container to said nozzle;
   said nozzle including a reservoir for holding a second quantity of odor modifying liquid;
   container liquid level detection means for continuously monitoring the liquid level in said container;
   nozzle liquid level detection means for continuously monitoring the liquid level in said nozzle reservoir; and
   control means including a DC power supply and an electronic programmable timer, said control means controlling operation of said liquid transport means in response to said container liquid level detection means, said nozzle liquid level detection means and said electronic programmable timer.

2. The system of claim 1, wherein said container liquid level detection means comprises a photon transmitter and a photon receiver.

3. The system of claim 1, wherein said nozzle liquid level detection means comprises a photon transmitter and a photon receiver.

4. The system of claim 1, wherein the liquid transferred to said nozzle is stored in said nozzle reservoir to facilitate the delivery of liquid vapor on demand.

5. The system of claim 1, wherein said nozzle further comprises an absorbent material housed in a tip of said nozzle for tertiary storage of the odor modifying liquid.

6. The system of claim 1, wherein said liquid transport means comprises a pump, tubing for connection of said pump between said container and said nozzle, and a pump control circuit.

7. The system of claim 1, wherein the time and date for dispensing of odor modifying vapors to said selected location is controlled by said electronic programmable timer.

\* \* \* \* \*